US012521260B2

(12) United States Patent
Cato et al.

(10) Patent No.: US 12,521,260 B2

(45) Date of Patent: Jan. 13, 2026

(54) RELEASABLE KNOTS FOR MEDICAL DEVICE DELIVERY

(71) Applicant: W. L. Gore & Associates, Inc., Newark, DE (US)

(72) Inventors: Milton C. Cato, Phoenix, AZ (US); Karl R. Chung, Phoenix, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 729 days.

(21) Appl. No.: 17/268,034

(22) PCT Filed: Aug. 31, 2018

(86) PCT No.: PCT/US2018/049053

§ 371 (c)(1),
(2) Date: Feb. 11, 2021

(87) PCT Pub. No.: WO2020/046364

PCT Pub. Date: Mar. 5, 2020

(65) Prior Publication Data

US 2021/0169669 A1 Jun. 10, 2021

(51) Int. Cl.
*A61F 2/95* (2013.01)
*A61F 2/07* (2013.01)

(52) U.S. Cl.
CPC .................. *A61F 2/95* (2013.01); *A61F 2/07* (2013.01); *A61F 2002/9511* (2013.01)

(58) Field of Classification Search
CPC ...... A61F 2/95; A61F 2/07; A61F 2002/9511; A61F 2/9522; A61F 2/011; A43C 11/008; A61M 2025/015; A61M 25/0147
See application file for complete search history.

(56) References Cited

U.S. PATENT DOCUMENTS

| | | | |
|---|---|---|---|
| 1,355,373 | A | 10/1920 | Dell |
| 1,506,432 | A | 8/1924 | Kimmel |
| 1,851,314 | A | 3/1932 | Knoche |
| 3,625,451 | A | 12/1971 | Anderson |
| 3,915,167 | A | 10/1975 | Waterman |
| 3,953,566 | A | 4/1976 | Gore |
| 4,187,390 | A | 2/1980 | Gore |

(Continued)

FOREIGN PATENT DOCUMENTS

| | | | |
|---|---|---|---|
| CN | 101554343 | A | 10/2009 |
| CN | 101780306 | A | 7/2010 |

(Continued)

OTHER PUBLICATIONS

International Preliminary Report on Patentability received for PCT Patent Application No. PCT/US2018/049057, mailed on Mar. 11, 2021, 9 pages.

(Continued)

*Primary Examiner* — Jerrah Edwards
*Assistant Examiner* — Kia Xiong White

(57) ABSTRACT

Various aspects of the present disclosure are directed toward apparatuses, systems and methods that include an implantable medical device an actuation line configured to steer the implantable medical device. The apparatuses, systems and methods may also include a releasable knot including portions of a tether to couple the actuation line to the implantable medical device.

20 Claims, 5 Drawing Sheets

(56) References Cited

U.S. PATENT DOCUMENTS

| | | | |
|---|---|---|---|
| 4,503,569 | A | 3/1985 | Dotter |
| 4,512,338 | A | 4/1985 | Balko et al. |
| 4,655,246 | A | 4/1987 | Phlipot et al. |
| 4,858,810 | A | 8/1989 | Intlekofer et al. |
| 4,990,155 | A | 2/1991 | Wilkoff |
| 5,035,706 | A | 7/1991 | Giantureo et al. |
| 5,037,427 | A | 8/1991 | Harada et al. |
| 5,147,370 | A | 9/1992 | Mcnamara et al. |
| 5,211,658 | A | 5/1993 | Clouse |
| 5,217,486 | A | 6/1993 | Rice et al. |
| 5,221,261 | A | 6/1993 | Termin et al. |
| 5,276,276 | A | 1/1994 | Gunn |
| 5,325,746 | A | 7/1994 | Anderson |
| 5,344,427 | A | 9/1994 | Cottenceau et al. |
| 5,491,704 | A | 2/1996 | Duron |
| 5,527,338 | A | 6/1996 | Purdy |
| 5,554,183 | A | 9/1996 | Nazari |
| 5,562,726 | A | 10/1996 | Chuter |
| 5,577,299 | A | 11/1996 | Thompson et al. |
| 5,693,083 | A | 12/1997 | Baker et al. |
| 5,707,376 | A | 1/1998 | Kavteladze et al. |
| 5,709,704 | A | 1/1998 | Nott et al. |
| 5,713,917 | A | 2/1998 | Leonhardt et al. |
| 5,713,948 | A | 2/1998 | Uflacker |
| 5,720,776 | A | 2/1998 | Chuter et al. |
| 5,725,552 | A | 3/1998 | Kotula et al. |
| 5,776,141 | A | 7/1998 | Klein et al. |
| 5,776,186 | A | 7/1998 | Uflacker |
| 5,782,909 | A | 7/1998 | Quiachon et al. |
| 5,843,162 | A | 12/1998 | Inoue |
| 5,873,906 | A | 2/1999 | Lau et al. |
| 5,904,703 | A | 5/1999 | Gilson |
| 5,961,546 | A | 10/1999 | Robinson et al. |
| 6,013,093 | A | 1/2000 | Nott et al. |
| 6,015,431 | A | 1/2000 | Thornton et al. |
| 6,019,785 | A | 2/2000 | Strecker |
| 6,042,588 | A | 3/2000 | Munsinger et al. |
| 6,042,602 | A | 3/2000 | Wells |
| 6,143,021 | A | 11/2000 | Staehle |
| 6,152,144 | A | 11/2000 | Esh et al. |
| 6,165,195 | A | 12/2000 | Wilson |
| 6,203,550 | B1 | 3/2001 | Olson |
| 6,214,025 | B1 | 4/2001 | Thistle et al. |
| 6,224,627 | B1 | 5/2001 | Armstrong et al. |
| 6,231,561 | B1 | 5/2001 | Frazier et al. |
| 6,231,581 | B1 | 5/2001 | Shank et al. |
| 6,231,589 | B1 | 5/2001 | Wessman et al. |
| 6,264,671 | B1 | 7/2001 | Stack et al. |
| 6,273,900 | B1 | 8/2001 | Nott et al. |
| 6,302,891 | B1 | 10/2001 | Nadal |
| 6,312,454 | B1 | 11/2001 | Stoeckel et al. |
| 6,322,585 | B1 | 11/2001 | Khosravi et al. |
| 6,328,727 | B1 | 12/2001 | Frazier et al. |
| 6,346,117 | B1 | 2/2002 | Greenhalgh |
| 6,352,561 | B1 | 3/2002 | Leopold et al. |
| 6,451,051 | B2 | 9/2002 | Drasler et al. |
| 6,475,234 | B1 | 11/2002 | Richter et al. |
| 6,485,513 | B1 | 11/2002 | Fan |
| 6,491,704 | B2 | 12/2002 | Gifford et al. |
| 6,524,335 | B1 | 2/2003 | Hartley et al. |
| 6,527,779 | B1 | 3/2003 | Rourke |
| 6,551,303 | B1 | 4/2003 | Van et al. |
| 6,551,350 | B1 | 4/2003 | Thornton et al. |
| 6,572,643 | B1 | 6/2003 | Gharibadeh |
| 6,572,646 | B1 | 6/2003 | Boylan et al. |
| 6,689,150 | B1 | 2/2004 | Vantassel et al. |
| 6,705,563 | B2 | 3/2004 | Luo et al. |
| 6,712,836 | B1 | 3/2004 | Berg et al. |
| 6,712,842 | B1 | 3/2004 | Gifford et al. |
| 6,730,108 | B2 | 5/2004 | Van et al. |
| 6,733,521 | B2 | 5/2004 | Chobotov et al. |
| 6,743,210 | B2 | 6/2004 | Hart et al. |
| 6,746,472 | B2 | 6/2004 | Frazier et al. |
| 6,755,854 | B2 | 6/2004 | Gillick et al. |
| 6,827,731 | B2 | 12/2004 | Armstrong et al. |
| 6,866,669 | B2 | 3/2005 | Buzzard et al. |
| 6,884,259 | B2 | 4/2005 | Tran et al. |
| 6,911,039 | B2 | 6/2005 | Shiu et al. |
| 6,926,732 | B2 | 8/2005 | Derus et al. |
| 6,939,352 | B2 | 9/2005 | Buzzard et al. |
| 6,945,990 | B2 | 9/2005 | Greenan |
| 6,949,113 | B2 | 9/2005 | Van et al. |
| 6,974,471 | B2 | 12/2005 | Van et al. |
| 6,994,092 | B2 | 2/2006 | Van et al. |
| 7,033,368 | B2 | 4/2006 | Rourke |
| 7,044,134 | B2 | 5/2006 | Khairkhahan et al. |
| 7,049,380 | B1 | 5/2006 | Chang et al. |
| 7,052,511 | B2 | 5/2006 | Weldon et al. |
| 7,066,951 | B2 | 6/2006 | Chobotov |
| 7,081,132 | B2 | 7/2006 | Cook et al. |
| 7,122,050 | B2 | 10/2006 | Randall et al. |
| 7,128,073 | B1 | 10/2006 | Van et al. |
| 7,147,657 | B2 | 12/2006 | Chiang et al. |
| 7,147,661 | B2 | 12/2006 | Chobotov et al. |
| 7,169,160 | B1 | 1/2007 | Middleman et al. |
| 7,198,636 | B2 | 4/2007 | Cully et al. |
| 7,208,003 | B2 | 4/2007 | Davis et al. |
| 7,252,680 | B2 | 8/2007 | Freitag |
| 7,331,992 | B2 | 2/2008 | Randall et al. |
| 7,396,359 | B1 | 7/2008 | Derowe et al. |
| 7,419,498 | B2 | 9/2008 | Opolski et al. |
| 7,462,675 | B2 | 12/2008 | Chang et al. |
| 7,555,034 | B2 | 6/2009 | Shin et al. |
| 7,566,336 | B2 | 7/2009 | Corcoran et al. |
| 7,572,289 | B2 | 8/2009 | Sisken et al. |
| 7,601,159 | B2 | 10/2009 | Ewers et al. |
| 7,611,528 | B2 | 11/2009 | Goodson et al. |
| 7,655,034 | B2 | 2/2010 | Mitchell et al. |
| 7,771,455 | B2 | 8/2010 | Ken |
| 7,815,591 | B2 | 10/2010 | Levine et al. |
| 7,837,724 | B2 | 11/2010 | Keeble et al. |
| 7,846,179 | B2 | 12/2010 | Belef et al. |
| 7,887,580 | B2 | 2/2011 | Randall et al. |
| 7,938,851 | B2 | 5/2011 | Olson et al. |
| 7,976,575 | B2 | 7/2011 | Hartley |
| 7,998,189 | B2 | 8/2011 | Koelbel et al. |
| 8,029,559 | B2 | 10/2011 | Sisken et al. |
| 8,043,356 | B2 | 10/2011 | Koelbel et al. |
| 8,048,440 | B2 | 11/2011 | Chang et al. |
| 8,062,349 | B2 | 11/2011 | Moore et al. |
| 8,080,032 | B2 | 12/2011 | Van et al. |
| 8,167,927 | B2 | 5/2012 | Chobotov |
| 8,231,650 | B2 | 7/2012 | Cully et al. |
| 8,241,346 | B2 | 8/2012 | Chobotov |
| 8,241,350 | B2 | 8/2012 | Randall et al. |
| 8,252,037 | B2 | 8/2012 | Styrc et al. |
| 8,257,431 | B2 | 9/2012 | Henderson et al. |
| 8,262,671 | B2 | 9/2012 | Osypka |
| 8,273,105 | B2 | 9/2012 | Cohen et al. |
| 8,287,583 | B2 | 10/2012 | Laduca et al. |
| 8,328,861 | B2 | 12/2012 | Martin et al. |
| 8,361,135 | B2 | 1/2013 | Dittman |
| 8,394,139 | B2 | 3/2013 | Roeder et al. |
| 8,424,166 | B2 | 4/2013 | Dorneman et al. |
| 8,449,595 | B2 | 5/2013 | Ouellette et al. |
| 8,469,990 | B2 | 6/2013 | Mcguckin et al. |
| 8,480,725 | B2 | 7/2013 | Rasmussen et al. |
| 8,523,897 | B2 | 9/2013 | Van et al. |
| 8,529,597 | B2 | 9/2013 | Linder et al. |
| 8,685,055 | B2 | 4/2014 | Vantassel et al. |
| 8,690,911 | B2 | 4/2014 | Miles et al. |
| 8,834,519 | B2 | 9/2014 | Van et al. |
| 8,870,947 | B2 | 10/2014 | Shaw |
| 8,968,384 | B2 | 3/2015 | Pearson et al. |
| 8,979,919 | B2 | 3/2015 | Goddard et al. |
| 8,986,363 | B2 | 3/2015 | Mchugo et al. |
| 9,060,895 | B2 | 6/2015 | Hartley et al. |
| 9,095,466 | B2 | 8/2015 | Norris et al. |
| 9,132,025 | B2 | 9/2015 | Aristizabal et al. |
| 9,254,204 | B2 | 2/2016 | Roeder et al. |
| 9,265,596 | B2 | 2/2016 | Shank et al. |
| 9,308,349 | B2 | 4/2016 | Rezac et al. |
| 9,351,858 | B2 | 5/2016 | Chobotov et al. |
| 9,364,359 | B2 * | 6/2016 | Crawford .................. A61F 2/95 |

(56) References Cited

U.S. PATENT DOCUMENTS 9,375,308 B2 6/2016 Norris
9,387,097 B2* 7/2016 Eblacas ..................... A61F 2/97
9,498,361 B2 11/2016 Roeder et al.
9,585,743 B2 3/2017 Cartledge et al.
9,585,774 B2 3/2017 Aristizabal et al.
9,681,968 B2 6/2017 Goetz et al.
9,700,701 B2 7/2017 Benjamin et al.
9,730,700 B2 8/2017 Herbowy et al.
9,770,322 B2 9/2017 Burkart et al.
9,782,282 B2 10/2017 Bloss et al.
9,782,284 B2 10/2017 Hartley et al.
9,877,858 B2 1/2018 Beard et al.
9,937,070 B2 4/2018 Skelton et al.
9,987,155 B1 6/2018 Sondreaal
11,123,174 B2 9/2021 Burkart et al.
11,324,615 B2 5/2022 Bloss et al.
12,076,227 B2 9/2024 Burkart et al.
2001/0034549 A1* 10/2001 Bartholf .................. A61F 2/966 623/1.12
2001/0037142 A1 11/2001 Stelter et al.
2002/0007208 A1 1/2002 Strecker
2002/0029076 A1 3/2002 Yee
2002/0029077 A1 3/2002 Leopold et al.
2002/0091439 A1 7/2002 Baker et al.
2002/0099431 A1 7/2002 Armstrong et al.
2002/0151953 A1 10/2002 Chobotov et al.
2003/0088305 A1 5/2003 Van et al.
2003/0098383 A1 5/2003 Luo et al.
2003/0149467 A1 8/2003 Linder et al.
2003/0181942 A1 9/2003 Sutton et al.
2004/0034366 A1 2/2004 Van et al.
2004/0054396 A1 3/2004 Hartley et al.
2004/0063805 A1 4/2004 Pacetti et al.
2004/0073289 A1 4/2004 Hartley
2004/0122503 A1 6/2004 Campbell et al.
2004/0138734 A1 7/2004 Chobotov et al.
2004/0143315 A1 7/2004 Bruun et al.
2005/0038470 A1 2/2005 Van et al.
2005/0049667 A1 3/2005 Arbefeuille et al.
2005/0070820 A1 3/2005 Boutillette et al.
2005/0080476 A1 4/2005 Gunderson et al.
2005/0085890 A1 4/2005 Rasmussen et al.
2005/0125031 A1 6/2005 Pipenhagen et al.
2005/0240257 A1 10/2005 Ishimaru et al.
2006/0004433 A1 1/2006 Greenberg et al.
2006/0015171 A1 1/2006 Armstrong
2006/0058833 A1 3/2006 Vancamp et al.
2006/0155366 A1 7/2006 Laduca et al.
2006/0198866 A1 9/2006 Chang et al.
2006/0254569 A1 11/2006 Chipman
2006/0264980 A1 11/2006 Khairkhahan et al.
2007/0016281 A1 1/2007 Melsheimer
2007/0066993 A1 3/2007 Kreidler
2007/0088424 A1 4/2007 Greenberg et al.
2007/0100427 A1 5/2007 Perouse
2007/0162048 A1 7/2007 Quinn et al.
2007/0167955 A1 7/2007 Arnault et al.
2007/0198077 A1 8/2007 Cully et al.
2007/0198078 A1 8/2007 Berra et al.
2007/0219467 A1 9/2007 Clark et al.
2007/0225797 A1 9/2007 Krivoruhko
2007/0248640 A1 10/2007 Karabey et al.
2007/0249980 A1 10/2007 Carrez et al.
2007/0255390 A1 11/2007 Ducke et al.
2007/0270891 A1 11/2007 McGuckin, Jr.
2008/0027529 A1 1/2008 Hartley et al.
2008/0039925 A1 2/2008 Ishimaru et al.
2008/0114440 A1 5/2008 Hlavka et al.
2008/0147111 A1 6/2008 Johnson et al.
2008/0178434 A1 7/2008 Bulanda
2008/0208329 A1 8/2008 Bishop et al.
2008/0269785 A1 10/2008 Lampropoulos et al.
2008/0294234 A1 11/2008 Hartley et al.
2009/0048656 A1 2/2009 Wen
2009/0054723 A1 2/2009 Khairkhahan et al.
2009/0062838 A1 3/2009 Brumleve et al.
2009/0082844 A1 3/2009 Zacharias et al.
2009/0099596 A1 4/2009 McGuckin et al.
2009/0099640 A1 4/2009 Weng
2009/0112249 A1 4/2009 Miles et al.
2009/0171386 A1 7/2009 Amplatz et al.
2009/0182405 A1 7/2009 Arnault De La Menardiere et al.
2009/0182407 A1 7/2009 Leanna et al.
2009/0182411 A1 7/2009 Irwin et al.
2009/0204198 A1 8/2009 Jensen et al.
2009/0216308 A1* 8/2009 Hartley ..................... A61F 2/95 623/1.11
2009/0259291 A1* 10/2009 Kolbel ...................... A61F 2/95 623/1.13
2009/0299449 A1 12/2009 Styrc
2010/0016943 A1 1/2010 Chobotov
2010/0023048 A1 1/2010 Mach
2010/0057195 A1 3/2010 Roeder et al.
2010/0082089 A1 4/2010 Quadri et al.
2010/0094394 A1 4/2010 Beach et al.
2010/0094401 A1 4/2010 Kolbel et al.
2010/0114290 A1 5/2010 Rasmussen et al.
2010/0211052 A1 8/2010 Brown et al.
2010/0280591 A1 11/2010 Shin et al.
2011/0034987 A1 2/2011 Kennedy
2011/0040366 A1 2/2011 Goetz et al.
2011/0054515 A1 3/2011 Bridgeman et al.
2011/0054519 A1 3/2011 Neuss
2011/0066221 A1 3/2011 White et al.
2011/0094401 A1 4/2011 Möhringer et al.
2011/0125252 A1 5/2011 Goddard et al.
2011/0130821 A1 6/2011 Styrc
2011/0288624 A1 11/2011 Roeder et al.
2011/0313503 A1 12/2011 Berra et al.
2012/0022630 A1 1/2012 Wuebbeling
2012/0022638 A1 1/2012 Leewood et al.
2012/0046652 A1 2/2012 Sokel
2012/0130473 A1 5/2012 Norris et al.
2012/0130474 A1 5/2012 Buckley
2012/0130475 A1 5/2012 Shaw
2012/0143305 A1 6/2012 Berra et al.
2012/0172965 A1 7/2012 Kratzberg et al.
2012/0172968 A1 7/2012 Chuter et al.
2012/0283773 A1 11/2012 Van et al.
2012/0296360 A1 11/2012 Norris et al.
2012/0323270 A1 12/2012 Lee
2013/0023981 A1 1/2013 Dierking et al.
2013/0046371 A1 2/2013 Greenberg et al.
2013/0073029 A1 3/2013 Shaw
2013/0123896 A1 5/2013 Bloss et al.
2013/0138138 A1 5/2013 Clark et al.
2013/0158647 A1 6/2013 Norris et al.
2013/0178889 A1 7/2013 Miles et al.
2013/0245666 A1 9/2013 Arsen et al.
2013/0245742 A1 9/2013 Norris
2013/0296912 A1 11/2013 Ottma
2014/0012303 A1 1/2014 Heipl
2014/0046360 A1 2/2014 Van et al.
2014/0180385 A1 6/2014 Majercak
2014/0194968 A1 7/2014 Zukowski
2014/0277412 A1 9/2014 Bortlein et al.
2014/0296908 A1 10/2014 Ottma et al.
2014/0296909 A1 10/2014 Heipl et al.
2014/0379019 A1 12/2014 Larsen et al.
2015/0005809 A1 1/2015 Ayres et al.
2015/0005810 A1 1/2015 Center et al.
2015/0051695 A1 2/2015 Shaw
2015/0305749 A1 10/2015 Alferness
2015/0313738 A1 11/2015 Cully et al.
2016/0256301 A1 9/2016 Roeder et al.
2016/0278782 A1* 9/2016 Anderson ........ A61B 17/12109
2016/0296352 A1 10/2016 Ryan et al.
2016/0331382 A1 11/2016 Center et al.
2017/0056153 A1 3/2017 Mnluan et al.
2017/0172724 A1 6/2017 Cartledge et al.
2017/0181751 A1 6/2017 Larsen et al.
2017/0281382 A1 10/2017 Lostetter et al.
2017/0367859 A1 12/2017 Bloss et al.
2018/0036113 A1 2/2018 Burkart et al.

(56) References Cited

U.S. PATENT DOCUMENTS

| | | | |
|---|---|---|---|
| 2018/0071123 | A1 | 3/2018 | Arbefeuille et al. |
| 2018/0071126 | A1 | 3/2018 | Beard et al. |
| 2019/0321207 | A1 | 10/2019 | Arbefeuille et al. |
| 2019/0388256 | A1 | 12/2019 | Chung et al. |
| 2021/0244553 | A1 | 8/2021 | Wiehn et al. |
| 2022/0151762 | A1 | 5/2022 | Burkart et al. |
| 2022/0211525 | A1 | 7/2022 | Bloss et al. |
| 2022/0395386 | A1 | 12/2022 | Beard et al. |
| 2024/0390132 | A1 | 11/2024 | Burkart et al. |

FOREIGN PATENT DOCUMENTS

| | | | |
|---|---|---|---|
| CN | 102413794 | A | 4/2012 |
| CN | 103347467 | A | 10/2013 |
| CN | 103930075 | A | 7/2014 |
| CN | 106102596 | A | 11/2016 |
| CN | 106344208 | A | 1/2017 |
| EP | 0664107 | A1 | 7/1995 |
| EP | 0679372 | A2 | 11/1995 |
| EP | 1441668 | B1 | 1/2008 |
| EP | 1915113 | B1 | 3/2010 |
| EP | 1358903 | B1 | 11/2011 |
| EP | 2481381 | A1 | 8/2012 |
| EP | 1474074 | B1 | 4/2014 |
| EP | 2749251 | B1 | 7/2016 |
| EP | 3064173 | A1 | 9/2016 |
| EP | 2956198 | B1 | 11/2017 |
| EP | 3278771 | A1 | 2/2018 |
| FR | 2896405 | A1 | 7/2007 |
| GB | 1355373 | A | 6/1974 |
| GB | 1506432 | A | 4/1978 |
| GB | 2344054 | A | 5/2000 |
| GB | 2448520 | A | 10/2008 |
| JP | 08-126704 | A | 5/1996 |
| JP | 09-309054 | A | 12/1997 |
| JP | 2001-506902 | A | 5/2001 |
| JP | 2002-503114 | A | 1/2002 |
| JP | 2002-518086 | A | 6/2002 |
| JP | 2003-502107 | A | 1/2003 |
| JP | 2004-167239 | A | 6/2004 |
| JP | 2004-188219 | A | 7/2004 |
| JP | 2007-518465 | A | 7/2007 |
| JP | 2011-511663 | A | 4/2011 |
| JP | 2011-511693 | A | 4/2011 |
| JP | 2011-516202 | A | 5/2011 |
| JP | 2014-501563 | A | 1/2014 |
| JP | 2014-501565 | A | 1/2014 |
| JP | 2014-502180 | A | 1/2014 |
| JP | 2014-533189 | A | 12/2014 |
| WO | 96/18361 | A1 | 6/1996 |
| WO | 97/48350 | A1 | 12/1997 |
| WO | 98/27894 | A1 | 7/1998 |
| WO | 99/65420 | A1 | 12/1999 |
| WO | 00/13613 | A1 | 3/2000 |
| WO | 01/21109 | A1 | 3/2001 |
| WO | 02/28317 | A2 | 4/2002 |
| WO | 03/34948 | A1 | 5/2003 |
| WO | 2003/101518 | A1 | 12/2003 |
| WO | 2005/070336 | A1 | 8/2005 |
| WO | 2005/072652 | A1 | 8/2005 |
| WO | 2006/007389 | A1 | 1/2006 |
| WO | 2007/092354 | A2 | 8/2007 |
| WO | 2008/047092 | A1 | 4/2008 |
| WO | 2008/063464 | A2 | 5/2008 |
| WO | 2009/102441 | A1 | 8/2009 |
| WO | 2009/126227 | A2 | 10/2009 |
| WO | 2009/148594 | A1 | 12/2009 |
| WO | 2010/001012 | A1 | 1/2010 |
| WO | 2010/024881 | A1 | 3/2010 |
| WO | 2010/041038 | A1 | 4/2010 |
| WO | 2010/044854 | A1 | 4/2010 |
| WO | 2010/063795 | A1 | 6/2010 |
| WO | 2010/081041 | A1 | 7/2010 |
| WO | 2010/090699 | A1 | 8/2010 |
| WO | 2010/105195 | A2 | 9/2010 |
| WO | 2011/031981 | A1 | 3/2011 |
| WO | 2011/062858 | A1 | 5/2011 |
| WO | 2012/068257 | A2 | 5/2012 |
| WO | 2012/065080 | A3 | 7/2012 |
| WO | 2012/136984 | A1 | 10/2012 |
| WO | 2012/174254 | A1 | 12/2012 |
| WO | 2013/040431 | A1 | 3/2013 |
| WO | 2013/074266 | A1 | 5/2013 |
| WO | 2013/137977 | A1 | 9/2013 |
| WO | 2015/132668 | A1 | 9/2015 |
| WO | 2018/005779 | A1 | 1/2018 |
| WO | 2018/165358 | A1 | 9/2018 |

OTHER PUBLICATIONS

International Search Report and Written Opinion received for PCT Patent Application No. PCT/US2018/049057, mailed on Apr. 23, 2019, 14 pages.

Hsu et al., The Impact of Bird-Beak Configuration on Aortic Remodeling of Distal Arch Pathology After Thoracic Endovascular Aortic Repair with the Zenith Pro-FormTX2 Thoracic Endograft, Journal of Vascular Surgery, 2013, pp. 1-9.

International Preliminary Report on Patentability received for PCT Patent Application No. PCT/US2018/049053, mailed on Mar. 11, 2021, 8 pages.

Thread. (n.d) American Heritage (r) Dictionary of the English Language, Fifth Edition. (2011). Retrieved Feb. 14, 2016 from http://www.thefreedictionary.com/thread.

Ueda, et al., Incomplete Endograft Apposition to the Aortic Arch: Bird-Beak Configuration Increases Risk of Endoleak Formation after Thoracic Endovascular Aortic Repair, Radiology: vol. 255: No. 2; May 2010, pp. 645-652.

* cited by examiner 202
206
208
210
212
214
216
316
400
112
x
y

RELEASABLE KNOTS FOR MEDICAL DEVICE DELIVERY

CROSS-REFERENCE TO RELATED APPLICATION

This application is a national phase application of PCT Application No. PCT/US2018/049053, internationally filed on Aug. 31, 2018, which is herein incorporated by reference in its entirety for all purposes.

FIELD

The present invention relates to medical devices and methods for treating an anatomical space (e.g., vessels) of the body. More specifically, the invention relates to methods, apparatuses, and systems that include an implantable medical device prosthesis that allows for accurate deployment in the anatomical space.

BACKGROUND

Disease of the vasculature is increasingly common. Treatment of the vasculature may be difficult because of the tortuous nature and complexity of the vasculature. Aortic dissections, for example, commonly begin at or near the aortic valve root and continue to the ascending aorta and the aortic arch, and may also affect the upper part of the descending aorta. Medical devices implanted at a diseased state may be used for treatment of aortic dissections, aneurysms, and other diseases of the vasculature.

It remains desirable to provide medical devices, systems and methods for repairing disease along the aorta (or other tortuous vessels) and also for repairing branches extending therefrom.

SUMMARY

According to one example ("Example 1"), a delivery system includes an implantable medical device; an actuation line configured to steer the implantable medical device during delivery thereof; a tether coupled to a portion of the implantable medical device arranged through the actuation line and configured to couple the actuation line to the implantable medical device; and a releasable knot including portions of the tether forming a first loop, a second loop, and a third loop with the third loop arranged through the second loop and the second loop arranged through the first loop and configured to couple the actuation line to the implantable medical device.

According to another example ("Example 2"), further to the delivery system of Example 1, the first loop is an eyelet formed by a first fold of the tether bonded at an overlapping portion of the first fold of the tether.

According to another example ("Example 3"), further to the delivery system of Example 2, the second loop is formed by a second fold of the tether and the third loop is formed by a third fold of the tether.

According to another example ("Example 4"), further to the delivery system of any one of Examples 1-3, the releasable knot is configured to release in response to tension applied to one end of the tether.

According to another example ("Example 5"), further to the delivery system of Example 1, the system also includes a fourth loop formed by a portion of the tether arranged through the third loop to form the releasable knot and the first loop is formed by a first fold of the tether, the second loop is formed by a second fold of the tether, the third loop is formed by a third fold of the tether, and the fourth loop is formed by a fourth fold of the tether.

According to another example ("Example 6"), further to the delivery system of Example 5, the releasable knot is configured to release in response to tension applied to both ends of the tether.

According to another example ("Example 7"), further to the delivery system of Example 5, a first end of the tether is arranged through the first loop, and a second end of the tether is arranged through the fourth loop, and the releasable knot is configured to release in response to tension applied to the second end of the tether.

According to another example ("Example 8"), further to the delivery system of any one of Examples 1-7, the releasable knot is configured to couple the actuation line to the implantable medical device without tension applied to the tether.

According to another example ("Example 9"), further to the delivery system of any one of Examples 1-8, the releasable knot is configured to resist separation between the actuation line and the implantable medical device in response to force applied to the actuation line.

According to one example ("Example 10"), a method of coupling an actuation line to an implantable medical device includes arranging the actuation line adjacent to the implantable medical device; routing a tether through an eyelet of the actuation line and coupling the tether to the implantable medical device; and forming a releasable knot that includes portions of the tether forming a first loop, a second loop, and a third loop with the third loop arranged through the second loop and the second loop arranged through the first loop and configured to couple the actuation line to the implantable medical device.

According to another example ("Example 11"), further to the method of Example 10, the method also includes visually inspecting the releasable knot to verify that the releasable knot couples the actuation line to the implantable medical device, and the releasable knot fails visual inspection by the releasable knot failing to maintain a knotted configuration and the releasable knot becoming at least partially unlooped.

According to another example ("Example 12"), further to the method of any one of Examples 10-11, forming the releasable knot includes forming the first loop by creating a first fold of the tether and bonding the tether at an overlapping portion of the first fold of the tether.

According to another example ("Example 13"), further to the method of any one of Examples 10-12, forming the releasable knot includes forming a fourth loop with a portion of the tether arranged through the third loop, wherein the first loop is formed by a first fold of the tether, the second loop is formed by a second fold of the tether, the third loop is formed by a third fold of the tether, and the fourth loop is formed by a fourth fold of the tether According to another example ("Example 14"), further to the method of any one of Examples 10-11, the method also includes releasing the releasable knot by applying tension to one or both ends of the tether.

According to another example ("Example 15"), further to the method of any one of Examples 10-14, the releasable knot is configured to resist separation between the actuation line and the implantable medical device in response to force applied to the actuation line.

According to another example ("Example 16"), a delivery system includes an implantable medical device; a line having an eyelet; and a tether coupled to the implantable medical device and arranged through the eyelet of the line and configured to couple the line to the implantable medical device and including portions of the tether having a first loop, a second loop, and a third loop with the third loop arranged through the second loop and the second loop arranged through the first loop and configured to couple the line to the implantable medical device.

According to another example ("Example 17"), further to the delivery system of Example 16, wherein the tether including the first, second, and third loops defines a releasable knot, the releasable knot is configured to resist separation between the line and the implantable medical device in response to force applied to the line.

According to another example ("Example 18"), further to the delivery system of Example 16, wherein the tether including the first, second, and third loops defines a releasable knot, the releasable knot is configured to couple the line to the implantable medical device without tension applied to the tether.

According to another example ("Example 19"), further to the delivery system of Example 16, the tether is configured to release the loops by applying tension to one or both ends of the tether.

According to another example ("Example 20"), further to the delivery system of Example 16, the system also includes a fourth loop formed by a portion of the tether arranged through the third loop, wherein the first loop is formed by a first fold of the tether, the second loop is formed by a second fold of the tether, the third loop is formed by a third fold of the tether, and the fourth loop is formed by a fourth fold of the tether.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
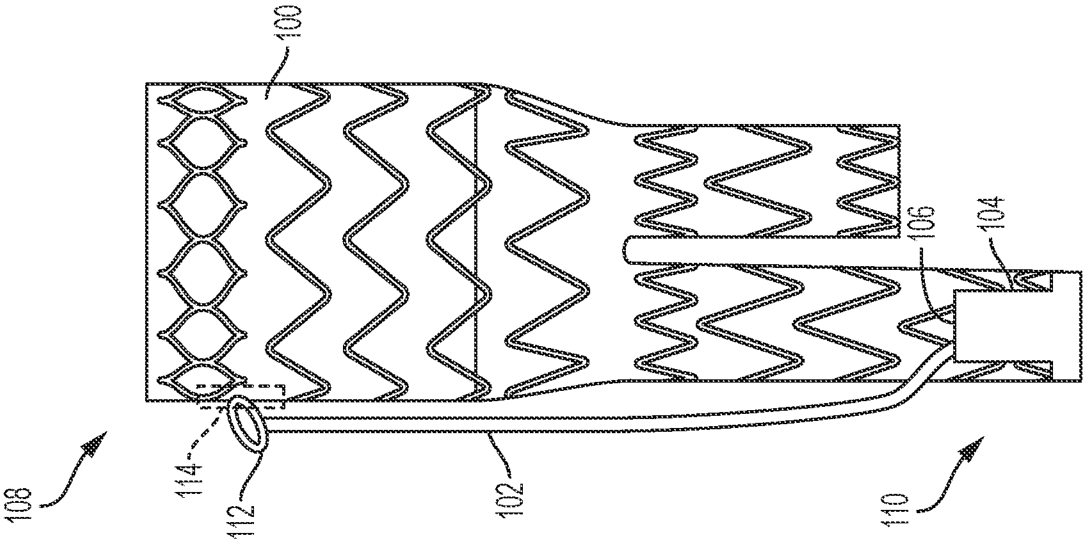
FIG. 1 shows an implantable medical device and an actuation line in accordance with an embodiment.

Persons skilled in the art will readily appreciate that various aspects of the present disclosure can be realized by any number of methods and apparatuses configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Various aspects of the present disclosure are directed toward apparatuses, systems, and methods that include an implantable medical device that may be used in treatment of the vasculature. The implantable medical device is delivered to the vasculature using a delivery system. In addition, the implantable medical devices described herein may be substantially cylindrical, include a bifurcation, or have any of a variety of features. Further, the implantable medical devices may be configured to conform to the vasculature into which the implantable medical device is implanted, low-profile in order to facilitate delivery of the implantable medical device using a minimally invasive procedure (e.g., via transcatheter techniques), and able to withstand forces and other stresses that occur once implanted in the vasculature.

The delivery system may be configured to position and/or steer the implantable medical device for placement in the vasculature. To position and or steer the implantable medical device, the delivery system may include a line that changes position of the implantable medical device in response to a user applying force to the line. The line may be releasably coupled to the implantable medical device (e.g., to permit removal of the line to avoid trauma to the vasculature after the implantable medical device is delivered and positioned). As discussed in further detail below, a tether may be used to releasably couple the line to the implantable medical device. The tether may be formed into a releasable knot that is easily manufacturable and facilitates proper deployment. The releasable knots discussed herein avoid entangling with the line during release. In other instances, the tether may also be used to releasably couple other lines to the implantable medical device.

FIG. 1 shows an implantable medical device 100 and a line 102 in accordance with various aspects of the present disclosure. The implantable medical device 100 is releasably coupled to a delivery system for delivery of the implantable medical device 100 to a target location within a patient's vasculature. The delivery system may include a catheter 104 that includes a leading end 106 and a trailing end (not shown in FIG. 1). The implantable medical device 100 may be arranged near the leading end 106 of the catheter 104. The catheter 104 may extend through a lumen of the implantable medical device 100 toward and past a proximal end 108 of the implantable medical device 100. The catheter 104 may also include a tip (not shown) at the leading end 106. As shown in FIG. 1, the implantable medical device 100 includes stent and graft components, although the implantable medical device can take a variety of forms including a stent, graft, bifurcated implantable medical device, heart valve, and the like.

The implantable medical device 100 includes a proximal end 108, a distal end 110, and a flow lumen extending therebetween. The proximal end 108 of the implantable medical device 100 may be considered the end of the implantable medical device 100 that is closest to the target location within the patient's vasculature. The line 102 may be coupled to the implantable medical device 100 at one or more locations. As shown in FIG. 1, the line 102 is attached adjacent to or near the proximal end 108 of the implantable medical device 100 and accessible to a user of the delivery system.

As shown, the line 102 is coupled to the implantable medical device 100 via at least one tether 112. The tether 112 may be arranged through a portion of the implantable medical device 100 and through the line 102 to couple the line 102 to the implantable medical device 100. In certain instances, and as shown in FIG. 1, the at least one tether 112 is arranged through the implantable medical device 100 near or adjacent to the proximal end 108 of the implantable medical device 100. The at least one tether 112 may be a single tether, as shown in FIG. 1.

In some instances, the implantable medical device 100 may include a patch 114 attached or coupled to a surface (e.g., an exterior surface) of the implantable medical device 100. The patch 114 may include a layer of graft material that forms a lumen between the surface of the implantable medical device 100 and the graft material. The tether 112 may be arranged through the patch 114 to couple the line 102 to the implantable medical device 100.

In certain instances, the line 102 is an actuation line 102 configured to steer the implantable medical device 100 during delivery thereof. The actuation line 102 may include a column strength such that a user operating the delivery system may apply force to the actuation line 102 and bidirectionally steer (e.g., proximally and distally relative to the target location within the patient's vasculature) the implantable medical device 100. For example, the actuation line 102 may have a stiffness that is greater than a stiffness of the tether 112. The stiffness of the actuation line 102 and/or the location to which the actuation line 102 is coupled to the implantable medical device 100 may facilitate deploying and arranging the implantable medical device 100 relative to the target location within the patient's vasculature. For example, the implantable medical device 100 may be configured to deploy at a tortuous vessel having a curvature with at least one inflection point. In certain instances, the actuation line 102 is configured to maintain the proximal end 108 of the implantable medical device 100 approximately perpendicular to the inflection point in the curvature of the tortuous vessel during delivery of the implantable medical device 100.

The actuation line 102 may be uncoupled or released from the implantable medical device 100 subsequent to the implantable medical device 100 being positioned and deployed at the target location within the patient's vasculature and removed from the patient. In certain instances, the tether 112 is configured to remain coupled or threaded through the implantable medical device 100 after the actuation line 102 is released or uncoupled from the implantable medical device 100. The actuation line 102 can include an eyelet or opening in a distal end through which the tether 112 is arranged. In addition, the tether 112 may be formed from a bio-absorbable material that dissolves to release or uncouple the actuation line 102 from the implantable medical device 100. In other instances, the tether 112 is configured to be removed or unthreaded to uncouple the actuation line 102 from the implantable medical device 100.

FIGS. 2A-D show an example tether 112 and steps in forming a releasable knot 200 with portions of the tether 112 in accordance with an embodiment. As explained in detail above with reference to FIG. 1, the tether 112 is coupled to a portion of an implantable medical device and arranged through a line (e.g., an actuation line) to couple the line to the implantable medical device. As shown in progressing through the steps shown in FIGS. 2A-D, the tether 112 forms a releasable knot, which is shown in a completed form in FIG. 2D. The tether 112 includes multiple loops in forming the releasable knot 200.

Figure 2D:
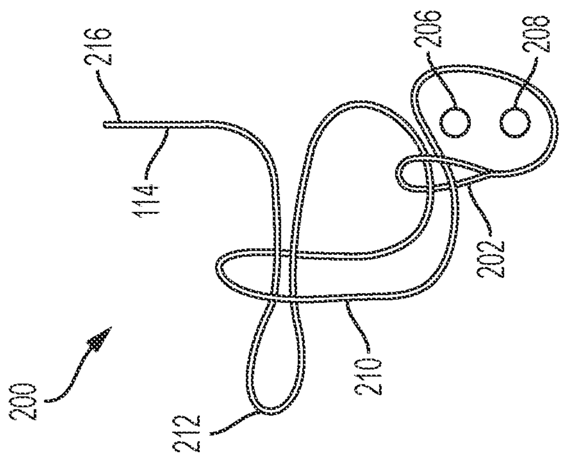
FIGS. 2A-2D show an example tether and steps in forming a releasable knot with portions of the tether in accordance with an embodiment.
Figure 2C:
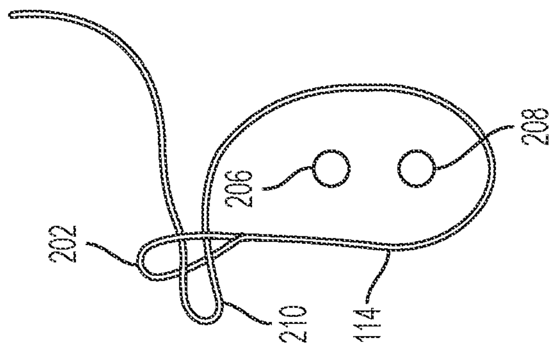
Figure 2B:
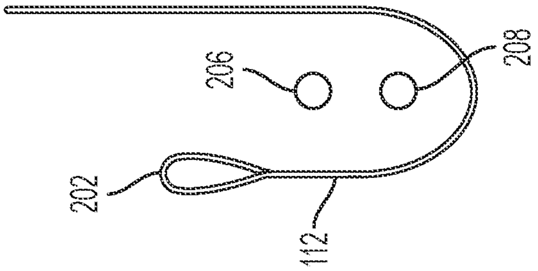
Figure 2A:
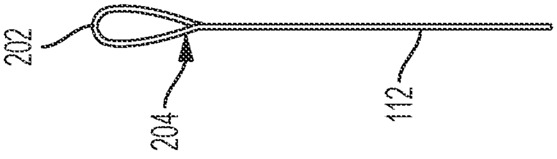

In certain instances, and as shown in FIG. 2A, the tether 112 includes first loop 202. The first loop 202 can be an eyelet that is formed by a first fold of the tether 112 that is bonded at an overlapping portion 204 of the first fold of the tether 112. The tether 112 may be bonded together by applying heat to bond the tether 112 to itself to form the first loop 202. The tether 112 is routed or arranged through a line and an implantable medical device to couple the line to the implantable medical device. For ease of illustration, element 206 is representative of one of the line and an implantable medical device and element 208 is representative of the other of the line and an implantable medical device. In certain instances, the element 206 may be the patch (shown in FIG. 1) or a hole in the implantable medical device and the element 208 may be an eyelet in the line.

As shown in FIG. 2B, the tether 112 is arranged about the element 206 and the element 208. In certain instances, the tether 112 is arranged through element 206 (the patch as shown in FIG. 1) and through an eyelet of the line. After being arranged through or about the element 206 and the element 208, the tether 112 may be folded to form a second loop 210 as shown in FIG. 2C. The second loop 210 of the tether 112 is then arranged through the first loop 202 of the tether 112.

In addition, and as shown in FIG. 2D, a third fold of the tether 112 may form a third loop 212. Subsequently, the third loop 212 is arranged through the second loop 210. Thus, the third loop 212 is arranged through the second loop 210, and the second loop 210 is arranged through the first loop 202 to form the releasable knot 200 as shown in FIG. 2D. In this configuration, the releasable knot 200 is configured to couple the actuation line to the implantable medical device.

After the multiple loops of the tether 112 are formed and arranged as discussed, tension may be applied to end 216 of the tether 112 to tighten the releasable knot 200. To release or untie the releasable knot 200, tension may be applied to the end 216.

Forming the releasable knot 200 in the manner discussed above may be manufacturable. In certain instances, the releasable knot 200 is formed or tied by hand. The steps to create the releasable knot 200 are relatively simple (e.g., not numerous, minimal crossover or loop formation in the tether 112). In addition, and in manufacturing or forming the releasable knot 200, it should be determined whether the releasable knot 200 is properly formed. The releasable knot 200 is properly formed when the releasable knot 200 couples the line to the implantable medical device. Forming the releasable knot 200 in the manner discussed above may also facilitate manufacturability by indicating whether the releasable knot 200 is properly formed. In this manner, the releasable knot 200 cannot be ineffectively formed. For example, if the steps in forming the releasable knot 200 are not followed, the releasable knot 200 will not maintain a knotted configuration (e.g., as shown in FIG. 2D) and the tether 112 will at least partially unloop. As a result, visually inspecting the releasable knot 200 to verify that the releasable knot 200 effectively couples the actuation line to the implantable medical device includes determining whether the releasable knot 200 maintains the knotted configuration or fails to do so.

In addition, the releasable knot 200 is configured to couple the actuation line to the implantable medical device without tension applied to the tether 112. After the releasable knot 200 is formed, tension does not need to be applied to hold the releasable knot 200 in the knotted configuration (e.g., as shown in FIG. 2D). An end 216 of the tether 112 may be coupled to a deployment handle (not shown) or a proximal portion of a catheter (e.g., as described above with reference to FIG. 1) such that a user may apply tension to the end 216 of the tether 112 or actuate a portion of the deployment handle that is coupled to the end 216 of the tether 112.

As noted above with reference to FIG. 1, the line (an actuation line) may steer the implantable medical device in response to a force applied to the actuation line. In certain instances, the force may be applied to the actuation line to bidirectionally steer (e.g., proximally and distally relative to the target location within the patient's vasculature) the implantable medical device. The releasable knot 200 is configured to maintain the knotted configuration to maintain the line coupled to the implantable medical device during steering. In certain instances, the releasable knot 200 is configured to resist separation between the (actuation) line and the implantable medical device in response to force applied to the actuation line. After the implantable medical device is aligned in a patient's vasculature (as noted above with reference to FIG. 1), the tether 112 is configured to release the second and third loops 210, 212 from the first loop 202 by applying tension to the end 216 of the tether 112.

FIGS. 3A-E show another example tether 112 and steps in forming a releasable knot 300 with portions of the tether 112 in accordance with an embodiment. As explained in detail above with reference to FIG. 1, the tether 112 is coupled to a portion of an implantable medical device and arranged through a line (e.g., an actuation line) to couple the line to the implantable medical device. As shown in progressing through the steps shown in FIGS. 3A-E, the tether 112 forms a releasable knot 300, which is shown in a completed form in FIG. 3E. The tether 112 includes multiple loops in forming the releasable knot 300.

Figures 3A, 3B, 3C, 3D, 3E:
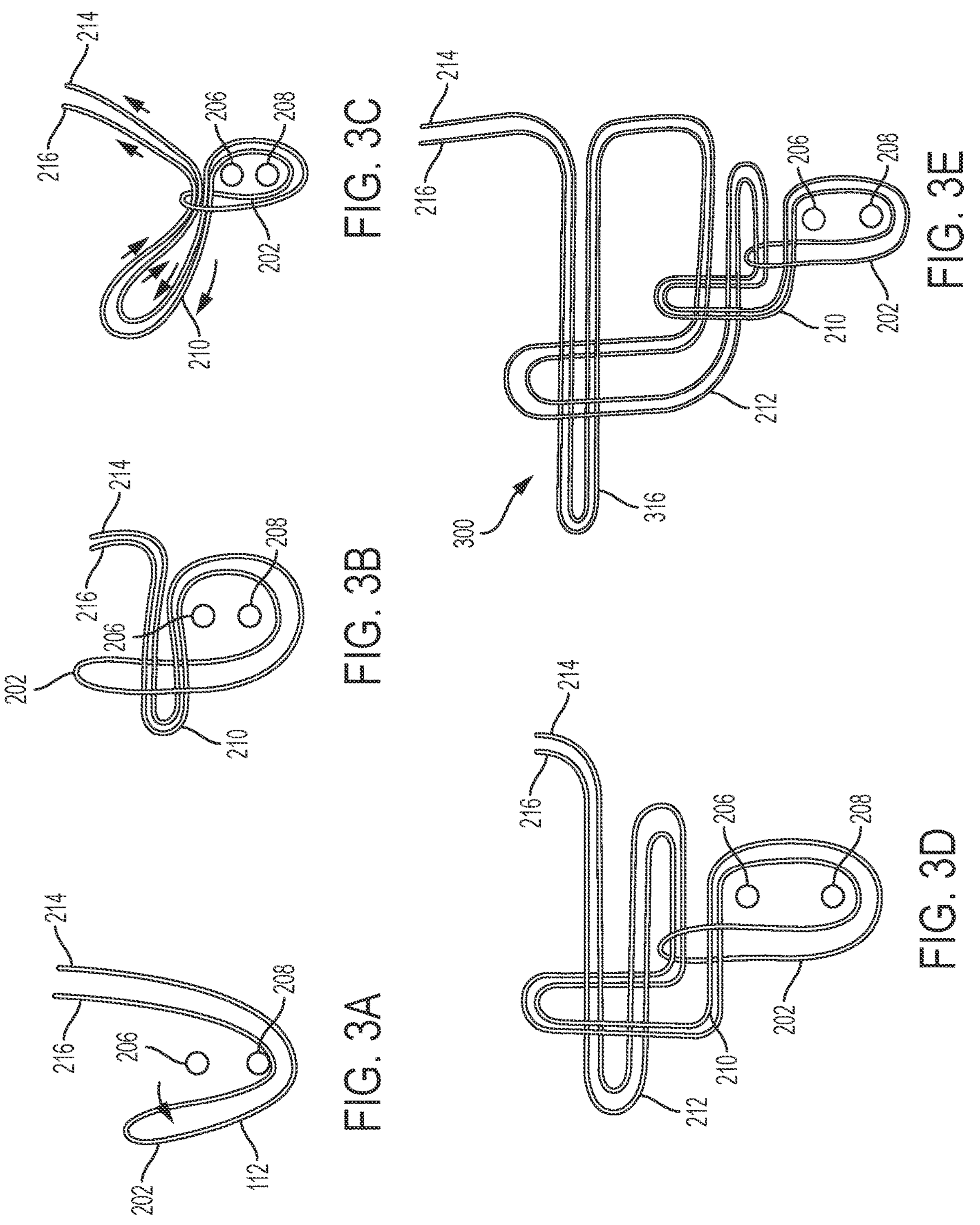
FIGS. 3A-3E show another example tether and steps in forming a releasable knot with portions of the tether in accordance with an embodiment.

In certain instances, and as shown in FIG. 3A, the tether 112 includes first loop 202. The first loop 202 may be formed by a first fold of the tether 112. The tether 112 is routed or arranged through a line and an implantable medical device to couple the line to the implantable medical device. Similar to the illustration in FIGS. 2A-D, element 206 is representative of one of the line and an implantable medical device and element 208 is representative of the other of the line and an implantable medical device. In certain instances, the element 206 may be the patch (shown in FIG. 1) or a hole in the implantable medical device and the element 208 may be an eyelet in the line. The tether 112 is arranged about the element 206 and the element 208. In certain instances, the tether 112 is arranged through element 206 (the patch as shown in FIG. 1) and through an eyelet of the line. After being arranged through or about the element 206 and the element 208, the tether 112 may be folded to form a second loop 210 as shown in FIG. 3B. The second loop 210 of the tether 112 is then arranged through the first loop 202 of the tether 112.

FIG. 3C shows a pathway for the tether 112 in forming the second loop 210. As shown in FIG. 2C, both portions of folded over tether 112 are used to form the second loop 210. In addition, and as shown in FIGS. 3A-E, each of the loops formed by the tether 112 include both portions of a folded over tether 112. For example, and as shown in FIG. 3D, a third fold of the tether 112 may form a third loop 212. The third loop 212 is then arranged through the second loop 210. Subsequently, the third loop 212 is arranged through the second loop 210. As shown in FIG. 3E, a fourth fold of the tether 112 may form a fourth loop 316. The fourth loop 316 is then arranged through the third loop 212.

After the fourth loop 316 is arranged through the third loop 212, tension may be applied to ends 214, 216 of the tether 112 to tighten and complete the releasable knot 300. To release or untie the releasable knot 300, tension may be applied to both of the ends 214, 216. After the releasable knot 300 is formed, tension does not need to be applied to hold the releasable knot 300 in the knotted configuration (e.g., as shown in FIG. 3E). One or both of the ends 214, 216 may be coupled to a deployment handle (not shown) or a proximal portion of a catheter (e.g., as described above with reference to FIG. 1) such that a user may apply tension to one of the ends 214, 216 of the tether 112 or actuate a portion of the deployment handle that is coupled to one of the ends 214, 216 of the tether 112.

Forming the releasable knot 300 in the manner discussed above may be manufacturable. The steps to create the releasable knot 300 are relatively simple (e.g., not numerous, minimal crossover or loop formation in the tether 112). In addition, and in manufacturing or forming the releasable knot 300, it should be determined whether the releasable knot 300 is properly formed. The releasable knot 300 is properly formed when the releasable knot 300 is able to couple the line to the implantable medical device. As a result, visually inspecting the releasable knot 300 to verify that the releasable knot 300 effectively couples the actuation line to the implantable medical device includes determining whether the releasable knot 300 maintains the knotted configuration or fails to do so.

As noted above with reference to FIG. 1, the line (an actuation line) may steer the implantable medical device in response to a force applied to the actuation line. In certain instances, the force may be applied to the actuation line to bidirectionally steer (e.g., proximally and distally relative to the target location within the patient's vasculature) the implantable medical device. The releasable knot 300 is configured to maintain the knotted configuration to maintain the line coupled to the implantable medical device during steering. In certain instances, the releasable knot 300 is configured to resist separation between the (actuation) line and the implantable medical device in response to force applied to the actuation line. After the implantable medical device is aligned in a patient's vasculature (as noted above with reference to FIG. 1), the tether 112 is configured to release the second and third loops 210, 212 from the first loop 202 by applying tension to the ends 214, 216 of the tether 112.

FIGS. 4A-F show another example tether and steps in forming a releasable knot with portions of the tether in accordance with an embodiment. As explained in detail above with reference to FIG. 1, the tether 112 is coupled to a portion of an implantable medical device and arranged through a line (e.g., an actuation line) to couple the line to the implantable medical device. As shown in progressing through the steps shown in FIGS. 4A-F, the tether 112 forms a releasable knot 400, which is shown in a completed form in FIG. 4F. As discussed in further detail below, the tether 112 forms a releasable knot 400 by way of multiple loops 202, 210, 212, and 316.

Figures 4A, 4B, 4C, 4D, 4E, 4F:
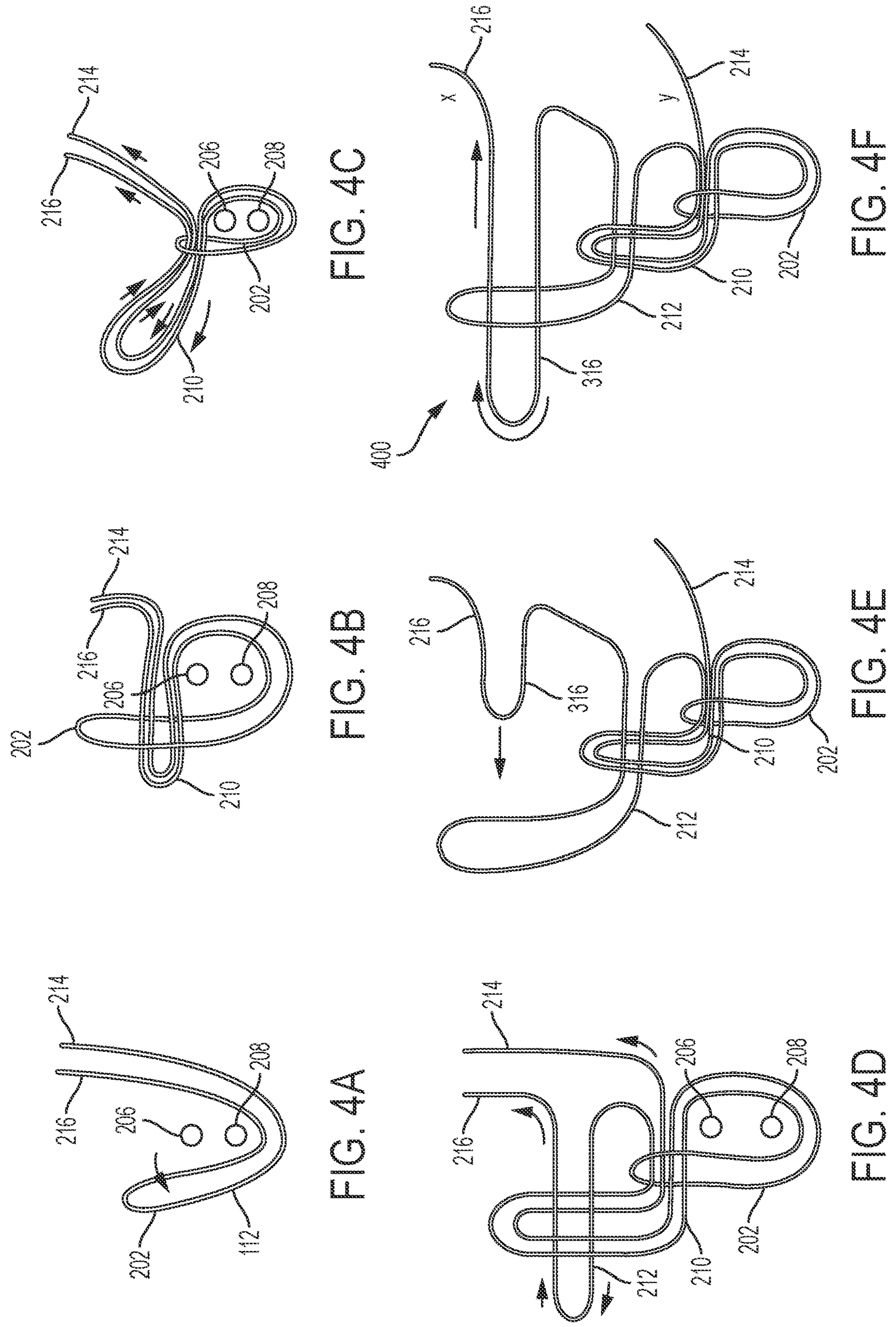
FIGS. 4A-4F show another example tether and steps in forming a releasable knot with portions of the tether in accordance with an embodiment.

In certain instances, and as shown in FIG. 4A, the tether 112 includes a first loop 202. The first loop 202 may be formed by a first fold of the tether 112. The tether 112 is routed or arranged through a line and an implantable medical device to couple the line to the implantable medical device. Similar to the illustration in FIGS. 2A-D and FIGS. 3A-E, element 206 is representative of one of the line and an implantable medical device and element 208 is representative of the other of the line and an implantable medical device. In certain instances, the element 206 may be the patch (shown in FIG. 1) or a hole in the implantable medical device and the element 208 may be an eyelet in the line. The tether 112 is arranged about the element 206 and the element 208. In certain instances, the tether 112 is arranged through element 206 (the patch as shown in FIG. 1) and through an eyelet of the line.

After being arranged through or about the element 206 and the element 208, the tether 112 may be folded to form a second loop 210 as shown in FIG. 4B. The second loop 210 of the tether 112 is then arranged through the first loop 202 of the tether 112. FIG. 4C shows a pathway for the tether 112 in forming the second loop 210. As shown in FIG. 4C, both portions of folded over tether 112 are used to form the second loop 210. Each of the first loop 202 and the second loop 210 formed by the tether 112 include both portions of a folded over tether 112. As shown in FIG. 4D, a third fold of the tether 112 that may form a third loop 212 includes one of the portions of the tether 112. As shown in FIG. 4D, end 214 of the tether 112 is arranged back through the first loop 202 while end 216 of the tether 112 is folded to form the third loop 212, which is arranged through the second loop 210.

Similar to the third loop 212 formed in the releasable knot 400, a fourth fold of the tether 112 may form a fourth loop 316 that includes the end 216 of the tether 112. The fourth loop 316 is then arranged through the third loop 212 as shown in FIGS. 4E-F. After the fourth loop 316 is arranged through the third loop 212, tension may be applied to ends 214, 216 of the tether 112 to tighten and complete the releasable knot 400.

To release or untie the releasable knot 400, tension may be applied to the end 216. In certain instances, the end 214 may be trimmed after the releasable knot 400 is formed. Further, the end 216 may be coupled to a deployment handle (not shown) or a proximal portion of a catheter (e.g., as described above with reference to FIG. 1) such that a user may apply tension to the end 216 of the tether 112 or actuate a portion of the deployment handle that is coupled to the end 216 of the tether 112. In addition, tension does not need to be applied to hold the releasable knot 400 in the knotted configuration (e.g., as shown in FIG. 4F).

Forming the releasable knot 400 in the manner discussed above may be manufacturable. The steps to create the releasable knot 400 are relatively simple (e.g., not numerous, minimal crossover or loop formation in the tether 112). In addition, and in manufacturing or forming the releasable knot 400, it should be determined whether the releasable knot 400 is properly formed. The releasable knot 400 is properly formed when the releasable knot 400 is able to couple the line to the implantable medical device. As a result, visually inspecting the releasable knot 400 to verify that the releasable knot 400 effectively couples the actuation line to the implantable medical device includes determining whether the releasable knot 400 maintains the knotted configuration or fails to do so.

As noted above with reference to FIG. 1, the line (an actuation line) may steer the implantable medical device in response to a force applied to the actuation line. The releasable knot 400 is configured to maintain the knotted configuration to maintain the line coupled to the implantable medical device during steering. In certain instances, the releasable knot 400 is configured to resist separation between the (actuation) line and the implantable medical device in response to force applied to the actuation line. After the implantable medical device is aligned in a patient's vasculature (as noted above with reference to FIG. 1), the tether 112 is configured to release the second and third loops 210, 212 from the first loop 202 by applying tension to one of the ends 214, 216 of the tether 112.

FIGS. 5A-E shows side view illustrations of expandable device angulation relative to a target location 500*a-e* in accordance with various aspects of the present disclosure. Each of FIGS. 5A-E show a side profile of a leading (or proximal) end 500*a-e* of an expandable device, consistent with various aspects of the present disclosure. In certain instances, the target location 500*a-e* may be at a tortuous vessel of a patient. The target location 500*a-e* into which the expandable device is implanted may have angulation (e.g., a curvature with at least one inflection point 504*a-e*). The target location 500*a-e* may be an angulated abdominal aortic aneurism (AAA), healthy tissue below the renal arteries, or other tortuous vessels. The releasable knots discussed herein enable actuation of the actuation wire at a location near a midpoint of the implantable device of distal to the midpoint (e.g., closer to the operator of the delivery system) on the implantable medical device.

Figure 5A:
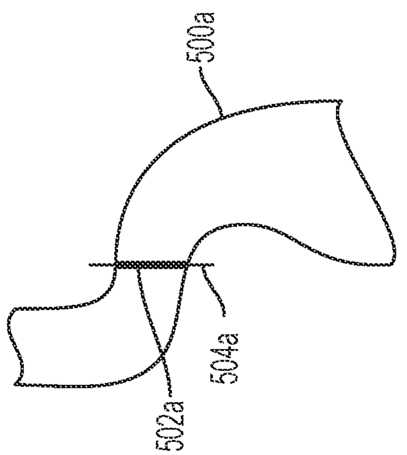
FIGS. 5A-5E show side view illustrations of expandable device angulation relative to a target location in accordance with various aspects of the present disclosure.
Figure 5B:
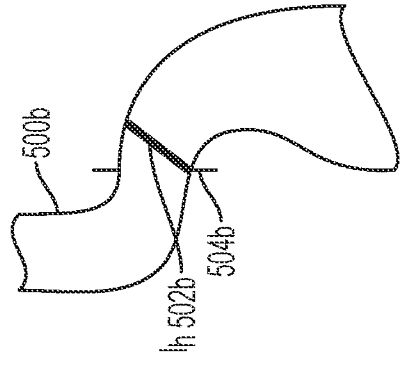
Figure 5C:
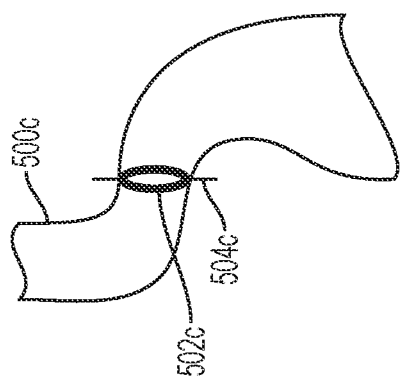
Figure 5D:
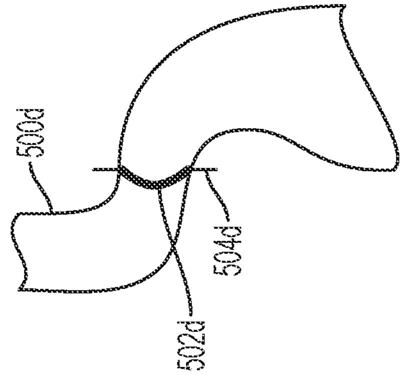
Figure 5E:
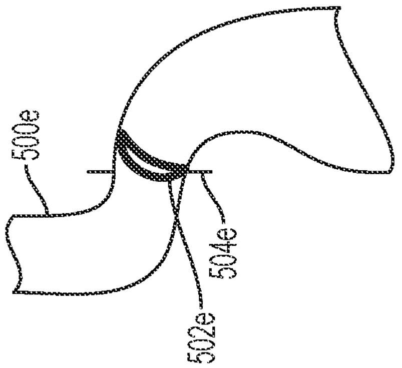

In certain instances, one of the ends 502*a-e* of the expandable device may be deployed perpendicular to the inflection point (e.g., of a heathy vessel tissue) in the curvature of the tortuous vessel during delivery of the expandable device. Non-perpendicularity may negatively affect the ability of the expandable device to seal against the target location 500*a-e*. FIG. 5A shows the leading (or proximal) end 502*a* deployed perpendicular to the inflection point 504*a*. In certain instances, perpendicularity of the expandable device may be a function of device flatness, angulation, and rotational alignment. FIG. 5B shows the leading (or proximal) end 502*b* of an expandable device angled relative to the inflection point 504*b* of the target location 500*b*. FIG. 5C shows the leading (or proximal) end 502*c* of an expandable device rotated relative to the inflection point 504*c* of the target location 500*c*. FIG. 5D shows the leading (or proximal) end 502*d* of an expandable device deformed relative to the inflection point 504*d* of the target location 500*d*. FIG. 5E shows the leading (or proximal) end 502*e* of an expandable device deformed or flat, rotated, and angled relative to the inflection point 504*e* of the target location 500*e*.

Device deployment and performance can be enhanced by steering the device to an appropriate location while maintaining one of the ends of the expandable device perpendicular to the target location 500*a-e* (e.g., curvature of a vessel with at least one inflection point 504*a-e*) during and after deployment. The actuation lines and arrangements thereof discussed herein facilitate maintaining the expandable device perpendicular during and after deployment (as shown in FIG. 5A) and mitigate against non-perpendicular, angled, or flat deployment (as shown in FIGS. 5B-E).

The lines discussed herein may be formed from metallic, polymeric or natural materials such as stainless steels, cobalt-chromium alloys and nitinol. Further, the lines can also be formed from high strength polymer fibers such as ultra high molecular weight polyethylene fibers (e.g., Spectra™., Dyneema Purity™., etc.) or aramid fibers (e.g., Technora™, etc.).

The graft components of the implantable medical device and/or the patch may be made up of any material which is suitable for use as a graft in the chosen body lumen and being resistant to expansion as discussed herein. The graft components may be composed of the same or different materials. Furthermore, the graft components may include multiple layers of material that can be the same material or different material. In one embodiment, said materials can be used in combination and assembled together to comprise a graft. The graft materials used in a stent graft can be extruded, coated or formed from wrapped films, or a combination thereof. Polymers, biodegradable and natural materials can be used for specific applications.

Examples of synthetic polymers include, but are not limited to, nylon, polyacrylamide, polycarbonate, polyformaldehyde, polymethylmethacrylate, polytetrafluoroethylene, polytrifluorochlorethylene, polyvinylchloride, polyurethane, elastomeric organosilicon polymers, polyethylene, polypropylene, polyurethane, polyglycolic acid, polyesters, polyamides, their mixtures, blends and copolymers are suitable as a graft material. In one embodiment, said graft is made from a class of polyesters such as polyethylene terephthalate including DACRON®. and MYLAR® and polyaramids such as KEVLAR®., polyfluorocarbons such as polytetrafluoroethylene (PTFE) with and without copolymerized hexafluoropropylene (TEFLON®. or GORE-TEX®.), and porous or nonporous polyurethanes. In another embodiment, said graft comprises expanded fluorocarbon polymers (especially PTFE) materials described in British Pat. Nos. 1,355,373; or 1,506,432 or in U.S. Pat. Nos. 3,953,566; 4,187,390; or 5,276,276, the entirety of which are incorporated by reference. Included in the class of preferred fluoropolymers are polytetrafluoroethylene (PTFE), fluorinated ethylene propylene (FEP), copolymers of tetrafluoroethylene (TFE) and perfluoro(propyl vinyl ether) (PFA), homopolymers of polychlorotrifluoroethylene (PCTFE), and its copolymers with TFE, ethylene-chlorotrifluoroethylene (ECTFE), copolymers of ethylene-tetrafluoroethylene (ETFE), polyvinylidene fluoride (PVDF), and polyvinyfluoride (PVF). Especially preferred, because of its widespread use in vascular prostheses, is expanded PTFE (ePTFE). In another embodiment, said graft comprises a combination of said materials listed above. In another embodiment, said graft is substantially impermeable to bodily fluids. Said substantially impermeable graft can be made from materials that are substantially impermeable to bodily fluids or can be constructed from permeable materials treated or manufactured to be substantially impermeable to bodily fluids (e.g. by layering different types of materials described above or known in the art). In another embodiment, said outermost tube comprises ePTFE. In another embodiment, said innermost tube comprises ePTFE. In another embodiment, said innermost and outermost tube comprises ePTFE film that has been wrapped into a tube. In another embodiment, said secondary stent is covered with any of the material disclosed herein or known in the art. In another embodiment, the secondary stent covering comprises ePTFE.

Additional examples of graft materials include, but are not limited to, vinylidinefluoride/hexafluoropropylene hexafluoropropylene (HFP), tetrafluoroethylene (TFE), vinylidenefluoride, 1-hydropentafluoropropylene, perfluoro (methyl vinyl ether), chlorotrifluoroethylene (CTFE), pentafluoropropene, trifluoroethylene, hexafluoroacetone, hexafluoroisobutylene, fluorinated poly(ethylene-co-propylene (FPEP), poly(hexafluoropropene) (PHFP), poly(chlorotrifluoroethylene) (PCTFE), poly(vinylidene fluoride (PVDF), poly(vinylidene fluoride-co-tetrafluoroethylene) (PVDF-TFE), poly(vinylidene fluoride-co-hexafluoropropene) (PVDF-HFP), poly(tetrafluoroethylene-co-hexafluoropropene) (PTFE-HFP), poly(tetrafluoroethylene-co-vinyl alcohol) (PTFE-VAL), poly(tetrafluoroethylene-co-vinyl acetate) (PTFE-VAC), poly(tetrafluoroethylene-co-propene) (PTFEP) poly(hexafluoropropene-co-vinyl alcohol) (PHFP-VAL), poly(ethylene-co-tetrafluoroethylene) (PETFE), poly (ethylene-co-hexafluoropropene) (PEHFP), poly(vinylidene fluoride-co-chlorotrifluoroe-thylene) (PVDF-CTFE), and combinations thereof, and additional polymers and copolymers described in U.S. Publication 2004/0063805, incorporated by reference herein in its entirety for all purposes. Additional polyfluorocopolymers include tetrafluoroethylene (TFE)/perfluoroalkylvinylether (PAVE). PAVE can be perfluoromethylvinylether (PMVE), perfluoroethylvinylether (PEVE), or perfluoropropylvinylether (PPVE), as described in U.S. Publication 2006/0198866 and U.S. Pat. No. 7,049,380, both of which are incorporated by reference herein for all purposes in their entireties. Other polymers and copolymers include, polylactide, polycaprolacton-glycolide, polyorthoesters, polyanhydrides; poly-aminoacids; polysaccharides; polyphosphazenes; poly(ether-ester) copolymers, e.g., polyethylene oxide (PEO)-Poly(I-lactide) (PLLA), or blends thereof, polydimethyl-siolxane; poly(ethylene-vingylacetate); acrylate based polymers or copolymers, e.g., poly(hydroxyethyl methylmethacrylate, polyvinyl pyrrolidinone; fluorinated polymers such as polytetrafluoroethylene; cellulose esters and any polymer and copolymers described in U.S. Publication 2004/0063805, incorporated by reference herein in its entirety.

The graft components, as discussed herein, may be attached to the self-expanding stent elements by using a coupling member that is generally a flat ribbon or tape having at least one generally flat surface. In certain instances, the tape member is made from ePTFE coated with an adhesive. The adhesive may be a thermoplastic adhesive. In certain instances, the thermoplastic adhesive may be fluorinated ethylene propylene (FEP). More specifically, an FEP-coated side of the ePTFE may face toward and contact an exterior surface of the self-expanding stent and graft component, thus attaching the self-expanding stent to the graft component. Materials and method of attaching a stent to the graft is discussed in U.S. Pat. No. 6,042,602 to Martin, incorporated by reference herein for all purposes in its entirety.

The stent component(s) discussed herein can be fabricated from a variety of biocompatible materials. These materials may include 316L stainless steel, cobalt-chromium-nickel-molybdenum-iron alloy ("cobalt-chromium"), other cobalt alloys such as L605, tantalum, Nitinol, or other biocompatible metals. In certain instances, as discussed in detail above, the stent (and graft) may be self-expanding. In other instances, the prosthesis may be balloon expandable.

The stent component(s) discussed herein may be constructed from a reasonably high strength material, i.e., one which is resistant to plastic deformation when stressed. In one embodiment, the stent component(s) comprise a line which is helically wound around a mandrel having pins arranged thereon so that the helical turns and undulations can be formed simultaneously. Other constructions may also be used. In certain instances, the stent component(s) are made from a super-elastic alloy. There are a variety of disclosures in which super-elastic alloys such as nitinol are used in stents. See for example, U.S. Pat. Nos. 4,503,569, to Dotter; U.S. Pat. No. 4,512,338, to Balko et al.; U.S. Pat. No. 4,990,155, to Wilkoff; U.S. Pat. No. 5,037,427, to Harada, et al.; U.S. Pat. No. 5,147,370, to MacNamara et al.; U.S. Pat. No. 5,211,658, to Clouse; and U.S. Pat. No. 5,221,261, to Termin et al.

A variety of materials variously metallic, super elastic alloys, such as Nitinol, are suitable for use in the stent component(s). Primary requirements of the materials are that they be suitably springy even when fashioned into very thin sheets or small diameter lines. Various stainless steels which have been physically, chemically, and otherwise treated to produce high springiness are suitable as are other metal alloys such as cobalt chrome alloys (e.g., ELGILOY®), platinum/tungsten alloys, and especially the nickel-titanium alloys generically known as "nitinol".

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. A delivery system comprising:

an implantable medical device;

an actuation line configured to bi-directionally steer the implantable medical device during delivery thereof;

a tether separate from the actuation line and coupled to a portion of the implantable medical device and to the actuation line, wherein the tether is configured to couple the actuation line to the implantable medical device; and a releasable knot including portions of the tether forming a first loop, a second loop, and a third loop with the third loop arranged through the second loop and the second loop arranged through the first loop and configured to couple the actuation line to the implantable medical device.

2. The delivery system of claim 1, wherein the first loop is an eyelet formed by a first fold of the tether bonded at an overlapping portion of the first fold of the tether.

3. The delivery system of claim 2, wherein the second loop is formed by a second fold of the tether and the third loop is formed by a third fold of the tether.

4. The delivery system of claim 1, wherein the releasable knot is configured to release in response to tension applied to one end of the tether.

5. The delivery system of claim 1, further comprising a fourth loop formed by a portion of the tether arranged through the third loop to form the releasable knot, wherein the first loop is formed by a first fold of the tether, the second loop is formed by a second fold of the tether, the third loop is formed by a third fold of the tether, and the fourth loop is formed by a fourth fold of the tether.

6. The delivery system of claim 5, wherein the releasable knot is configured to release in response to tension applied to both ends of the tether.

7. The delivery system of claim 5, wherein a first end of the tether is arranged through the first loop, and a second end of the tether is arranged through the fourth loop, and the releasable knot is configured to release in response to tension applied to the second end of the tether.

8. The delivery system of claim 1, wherein the releasable knot is configured to couple the actuation line to the implantable medical device without tension applied to the tether.

9. The delivery system of claim 1, wherein the releasable knot is configured to resist separation between the actuation line and the implantable medical device in response to force applied to the actuation line.

10. A method of coupling an actuation line to an implantable medical device, the method including:

arranging the actuation line adjacent to the implantable medical device;

routing a tether through an eyelet of the actuation line to fixedly couple the tether to the actuation line, wherein the tether is coupled to the implantable medical device at a proximal end of the implantable medical device; and forming a releasable knot that includes portions of the tether forming a first loop, a second loop, a third loop, and a fourth loop with the fourth loop arranged through the third loop, the third loop arranged through the second loop, and the second loop arranged through the first loop and configured to couple the actuation line to the implantable medical device at the proximal end of the implantable medical device.

11. The method of claim 10, further including visually inspecting the releasable knot to verify that the releasable knot couples the actuation line to the implantable medical device, and the releasable knot fails visual inspection by the releasable knot failing to maintain a knotted configuration and the releasable knot becoming at least partially unlooped.

12. The method of claim 10, wherein forming the releasable knot includes forming the first loop by creating a first fold of the tether and bonding the tether at an overlapping portion of the first fold of the tether.

13. The method of claim 10, wherein forming the releasable knot includes forming a fourth loop with a portion of the tether arranged through the third loop, wherein the first loop is formed by a first fold of the tether, the second loop is formed by a second fold of the tether, the third loop is formed by a third fold of the tether, and the fourth loop is formed by a fourth fold of the tether.

14. The method of claim 13, further comprising releasing the releasable knot by applying tension to both ends of the tether.

15. The method of claim 10, wherein the releasable knot is configured to resist separation between the actuation line and the implantable medical device in response to force applied to the actuation line.

16. A delivery system comprising:

an implantable medical device;

a line having an eyelet and a distal end configured to be tensioned by a user;

and a tether coupled to the implantable medical device and arranged through the eyelet of the line and configured to couple the line to the implantable medical device, wherein when the distal end of the line is tensioned by the user the line is configured to pull the tether and steer the implantable medical device, wherein the tether includes portions having a first loop, a second loop, a third loop, and a fourth loop with the fourth loop arranged through the third loop, the third loop arranged through the second loop, and the second loop arranged through the first loop to define a releasable knot and configured to couple the line to the implantable medical device.

17. The delivery system of claim 16, wherein the releasable knot is configured to resist separation between the line and the implantable medical device in response to force applied to the line.

18. The delivery system of claim 16, wherein the releasable knot is configured to couple the line to the implantable medical device without tension applied to the tether.

19. The delivery system of claim 16, wherein the first loop is formed by a first fold of the tether, the second loop is formed by a second fold of the tether, the third loop is formed by a third fold of the tether, and the fourth loop is formed by a fourth fold of the tether.

20. The delivery system of claim 19, wherein the tether is configured to release the loops by applying tension to both ends of the tether.

* * * * *